US009920128B2

(12) United States Patent
Lin et al.

(10) Patent No.: US 9,920,128 B2
(45) Date of Patent: Mar. 20, 2018

(54) SYNTHETIC ANTISERUM FOR RAPID-TURNAROUND THERAPIES

(71) Applicant: The Johns Hopkins University, Baltimore, MD (US)

(72) Inventors: Jeffrey S. Lin, Silver Spring, MD (US); Andrew B. Feldman, Columbia, MD (US); Jared D. Evans, Ellicott City, MD (US); Joshua T. Wolfe, Bethesda, MD (US); David Weitz, Bolton, MA (US); John Heyman, Somerville, MA (US); Andrew S. Pekosz, Towson, MD (US)

(73) Assignee: The Johns Hopkins University, Baltimore, MD (US)

( * ) Notice: Subject to any disclaimer, the term of this patent is extended or adjusted under 35 U.S.C. 154(b) by 56 days.

(21) Appl. No.: 15/001,349

(22) Filed: Jan. 20, 2016

(65) Prior Publication Data

US 2016/0215282 A1 Jul. 28, 2016

Related U.S. Application Data

(60) Provisional application No. 62/108,676, filed on Jan. 28, 2015.

(51) Int. Cl.
*C07K 16/00* (2006.01)
*C07K 16/30* (2006.01)

(52) U.S. Cl.
CPC .............. *C07K 16/30* (2013.01); *C07K 16/00* (2013.01)

(58) Field of Classification Search
None
See application file for complete search history.

(56) References Cited

PUBLICATIONS

Mazutis et al. Single-cell analysis and sorting using droplet-based microfluidics. Nat Protoc. May 2013;8(5):870-91.*
Corti et al. A neutralizing antibody selected from plasma cells that binds to group 1 and group 2 influenza A hemagglutinins. Science. Aug. 12, 2011;333(6044):850-6.*
(Continued)

*Primary Examiner* — Michelle S Horning
(74) *Attorney, Agent, or Firm* — Todd R. Farnsworth

(57) ABSTRACT

A method for synthesizing an antiserum for rapid-turnaround therapies includes collecting antibody-secreting cells from a test subject, wherein the test subject has been exposed to a target biological agent and has produced an antibody response; selecting a subset of the antibody-secreting cells, the subset of the antibody-secreting cells producing antibodies that neutralize the target biological agent; generating variable-region-coding DNA sequences from the antibodies that neutralize the target biological agent; tagging amplicons of the variable-region-coding DNA sequences with unique nucleic acid identifiers to associate the variable-region-coding DNA sequences derived from individual ones of the subset of the antibody-secreting cells; analyzing antibody-type distribution in a natural immune response; synthesizing antibodies from the variable-region-coding DNA sequences to form synthetic antibodies; and mixing the synthetic antibodies in a proportion equal to the antibody-type distribution in the natural immune response to form the antiserum.

10 Claims, 7 Drawing Sheets

(56) References Cited

PUBLICATIONS

Georgiou et al. The promise and challenge of high-throughput sequencing of the antibody repertoire. Nat Biotechnol. Feb. 2014;32(2):158-68.*

Greenspan. Design Challenges for HIV-1 Vaccines Based on Humoral Immunity. Front Immunol. Jul. 16, 2014;5:335.*

* cited by examiner

SYNTHETIC ANTISERUM FOR RAPID-TURNAROUND THERAPIES

CROSS-REFERENCE TO RELATED APPLICATION

This application claims the benefit of U.S. Provisional Application No. 62/108,676 filed on Jan. 28, 2015, the entire contents of which are hereby incorporated herein by reference.

TECHNICAL FIELD

Example embodiments relate generally to methods for rapidly synthesizing antisera.

BACKGROUND

Traditional antiserum treatments concentrate serum antibodies from other immune humans or animals. Antiserum derived from human, bovine and equine sources has been used or proposed. The antiserum may contain many constituents that are not desired: non-specific antibodies, infectious agents such as viruses, and immunoregulatory molecules that may cause adverse responses. Using antiserum to establish therapeutic levels of antibody in patient blood runs the risk of serum sickness complications due to potentially undesirable components of antiserum.

In contrast, defined synthetic antiserum includes only selected antibodies identified in blood products and produced under controlled conditions and formulation processing, eliminating undesired non-specific binding antibodies as well as other contaminations in the original serum. Traditional synthetic antibody therapies are designed based on a constructive design philosophy that includes one or very limited numbers of functionally therapeutic antibodies. The challenge in this design is that the effect of each candidate antibody are generally characterized independently, requiring considerable time and expense. This testing, performed in in vitro cultures does not always predict performance in an animal model due to interactions with other immune system responses such as antibody dependent cell-mediated cytotoxicity (ADCC), antibody dependent enhancement (ADE), and the innate immune system. Furthermore, testing in animal models does not necessarily predict performance in humans due to different physiologies between species. Thus, developing candidate mixtures of antibodies in a constructive design is time consuming and unpredictable. In addition, when the targeted agent is a virus capable of rapid evolution in response to selection pressures such as antibody binding and neutralization, a mixture of only a few antibodies poses the very real risk of not being effective against all viral variants, thereby enabling the emergence of viral strains that are immune to the antibody mixture.

Therefore there at least remains a need in the art for an efficient and cost-effective method for synthesizing an antiserum that provides protection and treatment for a biological agent and also replicates the natural immune response.

BRIEF SUMMARY

One or more example embodiments may address one or more of the aforementioned problems. Certain example embodiments provide a method for synthesizing an antiserum for rapid-turnaround therapies. In accordance with certain embodiments, the method may comprise collecting antibody-secreting cells from a test subject, wherein the test subject has been exposed to a target biological agent and has produced an antibody response; selecting a subset of the antibody-secreting cells, the subset of the antibody-secreting cells producing antibodies that neutralize the target biological agent; generating variable-region-coding DNA sequences from the antibodies that neutralize the target biological agent; tagging amplicons of the variable-region-coding DNA sequences with unique nucleic acid identifiers to associate the variable-region-coding DNA sequences derived from individual ones of the subset of the antibody-secreting cells; analyzing antibody-type distribution in a natural immune response; synthesizing antibodies from the variable-region-coding DNA sequences to form synthetic antibodies; and mixing the synthetic antibodies in a proportion equal to the antibody-type distribution in the natural immune response to form the antiserum.

In another aspect, a method for mitigating effects of a target biological agent on an affected subject is provided. The method may comprise synthesizing an antiserum for rapid-turnaround therapies and administering the antiserum to the affected subject in need thereof. In such embodiments, synthesizing the antiserum may comprise collecting antibody-secreting cells from a test subject, wherein the test subject has been exposed to a target biological agent and has produced an antibody response; selecting a subset of the antibody-secreting cells, the subset of the antibody-secreting cells producing antibodies that neutralize the target biological agent; generating variable-region-coding DNA sequences from the antibodies that neutralize the target biological agent; tagging amplicons of the variable-region-coding DNA sequences with unique nucleic acid identifiers to associate the variable-region-coding DNA sequences derived from individual ones of the subset of the antibody-secreting cells; analyzing antibody-type distribution in a natural immune response; synthesizing antibodies from the variable-region-coding DNA sequences to form synthetic antibodies; and mixing the synthetic antibodies in a proportion equal to the antibody-type distribution in the natural immune response to form the antiserum.

BRIEF DESCRIPTION OF THE DRAWING(S)

Having thus described example embodiments in general terms, reference will now be made to the accompanying drawings, which are not necessarily drawn to scale, and wherein:

FIG. 1 illustrates an overview of a method for synthesizing an antiserum for rapid turnaround therapies according to an example embodiment;

FIG. 2 illustrates a block diagram of a method for synthesizing an antiserum for rapid turnaround therapies including the optional steps of priming the antibody response in the test subject, boosting the natural immune response in the test subject, challenging the natural immune response in the test subject, and validating neutralization properties of the antiserum according to an example embodiment;

DETAILED DESCRIPTION

Figure 1:
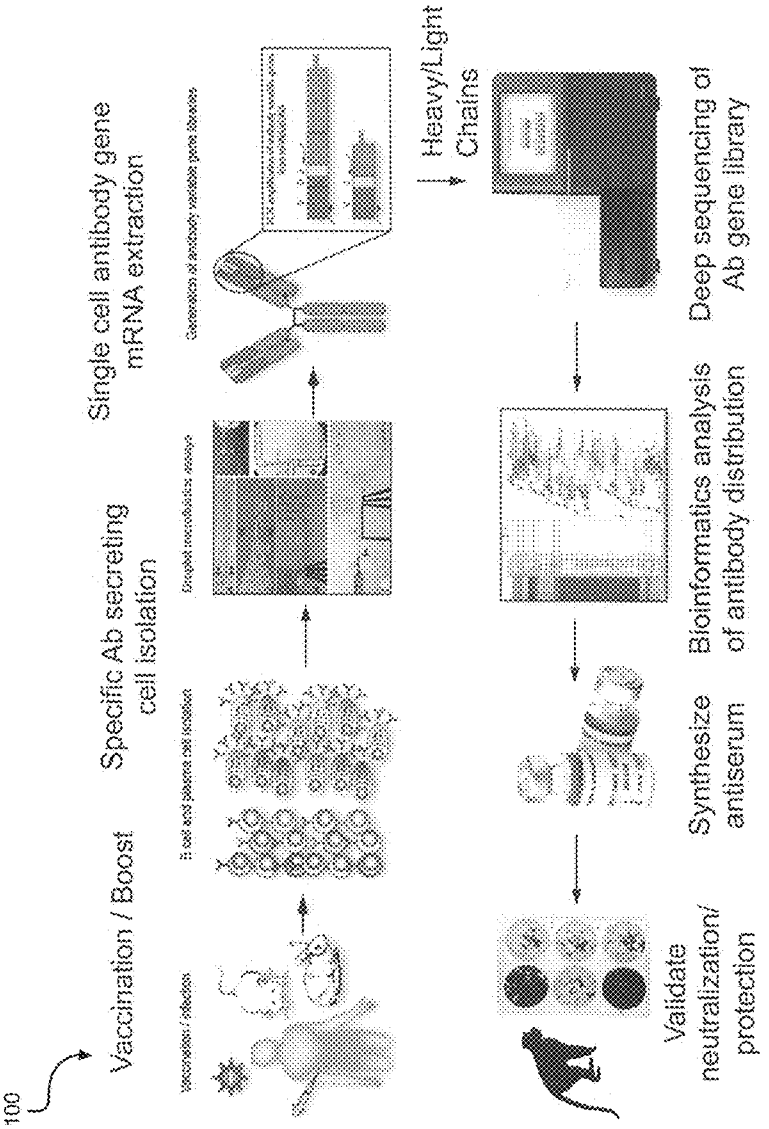

Some example embodiments now will be described more fully hereinafter with reference to the accompanying drawings, in which some, but not all embodiments are shown. Indeed, the examples described and pictured herein should not be construed as being limiting as to the scope, applicability, or configuration of the present disclosure. Rather, these example embodiments are provided so that this disclosure will satisfy applicable legal requirements. Like reference numeral refer to like elements throughout. As used in the specification, and in the appended claims, the singular forms “a”, “an”, “the”, include plural referents unless the context clearly dictates otherwise.

Certain example embodiments provide a method for synthesizing an antiserum for rapid-turnaround therapies. For instance, this method may provide, for example, an affordable and efficient manner for generating antisera that provide protection and treatment against a target biological agent while also replicating the natural immune response (including, for example, antibody dependent cell-mediated cytotoxicity and/or the like) to that target biological agent in a healthy individual. As such, for example, this method may permit rapid development of antisera in a single process in times of health crisis, for instance, for high mortality emergent diseases, orphaned diseases, and/or the like. In this regard, the method may be used to produce a prophylaxis for pre- and post-exposure to infectious agents, a treatment for infectious disease, a neutralizing agent for exposure to toxins, and/or the like that can be introduced either directly or produced by an infectious agent. Moreover, the method may be used in combination with any other therapies which utilize the health benefits of antibodies as understood by one of ordinary skill in the art.

Although particular viruses, bacteria, toxins, prions and/or the like are frequently referenced throughout this disclosure, these particular biological agents serve only as exemplary embodiments, and, as such, this disclosure should not be limited to such biological agents, as other exemplary embodiments could be applicable to a wide variety of protein-based biological agents. Furthermore, although humans and livestock are frequently referenced to throughout this disclosure, humans and livestock serve only as exemplary applications, and this disclosure is not so limited.

As used herein, the terms “antibody” and “antibodies” may comprise a glycoprotein substantially encoded by an immunoglobulin gene or immunoglobulin genes, or fragments thereof, which specifically recognize and bind foreign molecules called antigens. The recognized immunoglobulin genes include the kappa, lambda, alpha, gamma, delta, epsilon, and mu constant region genes, as well as the immunoglobulin variable region genes. Antibodies include fragments, such as Fab', $F(ab)_2$, Fabc, and Fv fragments. Fab fragments are the antigen-binding domains of an antibody molecule. Fab fragments can be prepared by papain digestions of whole antibodies. Fv fragments are the minimal fragment (~30 kDa) that still contains the whole antigen-binding site of a whole IgG antibody. Fv fragments are composed of both the variable heavy chain ($V_H$) and variable light chain ($V_L$) domains. This heterodimer, called Fv fragment (for fragment variable) is still capable of binding the antigen. The term “antibody,” as used herein, also includes antibody fragments either produced by the modification of whole antibodies or those synthesized de novo using recombinant DNA methodologies, and further includes “humanized” antibodies made by now conventional techniques.

The terms “antiserum” and “antisera”, as used herein, may comprise blood serum that contains antibodies, as antitoxins or agglutinins, obtained by inoculation of animals and used for injection into other animals to provide immunity to a specific viral infection. Specifically, inoculating one animal with the infections agent, or “antigen”, induces B-lymphocytes to produce IgG immunoglobulins specific for the antigen. The antibodies in the antiserum bind the antigen in the host, and the host immune system then recognizes foreign agents bound to the antibodies and triggers a more robust immune response.

I. Method for Synthesizing an Antiserum for Rapid-Turnaround Therapies

In some example embodiments, a method for synthesizing an antiserum for rapid-turnaround therapies is provided. For instance, this method may provide, for example, an affordable and efficient manner for generating antisera that provide protection and treatment against a target biological agent while also replicating the natural immune response (including, for example, antibody dependent cell-mediated cytotoxicity and/or the like) to that target biological agent in a healthy individual. In general, methods for synthesizing an antiserum for rapid-turnaround therapies may include collecting antibody-secreting cells from a test subject, wherein the test subject has been exposed to a target biological agent and has produced an antibody response; selecting a subset of the antibody-secreting cells, the subset of the antibody-secreting cells producing antibodies that neutralize the target biological agent; generating variable-region-coding DNA sequences from the antibodies that neutralize the target biological agent; tagging amplicons of the variable-region-coding DNA sequences with unique nucleic acid identifiers to associate the variable-region-coding DNA sequences derived from individual ones of the subset of the antibody-secreting cells; analyzing antibody-type distribution in a natural immune response; synthesizing antibodies from the variable-region-coding DNA sequences to form synthetic antibodies; and mixing the synthetic antibodies in a proportion equal to the antibody-type distribution in the natural immune response to form the antiserum.

Figure 2:
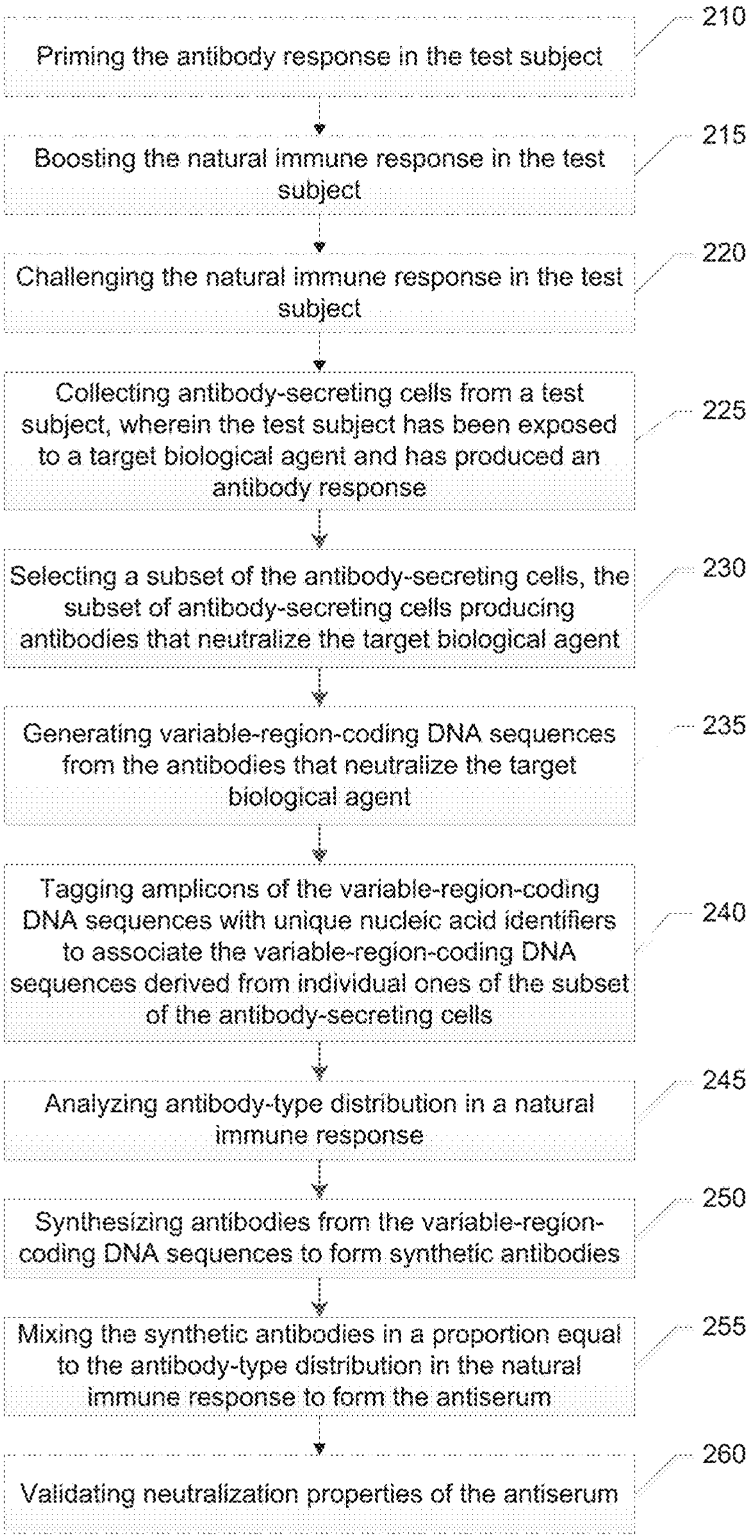

FIGS. 1 and 2, for example, illustrate a method for synthesizing an antiserum for rapid turnaround therapies according to an example embodiment. As shown in FIG. 1, for instance, the overview 100 provides for rapid formulation of a replicated effective vaccine response via high-throughput functional screening and testing. As shown in FIG. 2, the exemplary method may include the initial optional steps of priming the antibody response in the test subject at operation 210, boosting the natural immune response in the test subject at operation 215, and challenging the natural immune response in the test subject at operation 220. Next, the exemplary method continues by collecting antibody-secreting cells from the test subject at operation 225, as the test subject has been exposed to a target biological agent and has produced an antibody response. The exemplary method may continue by selecting a subset of the antibody-secreting cells that produce antibodies that neutralize the target biological agent at operation 230, generating variable-region-coding DNA sequences from the antibodies that neutralize the target biological agent at operation 235, tagging amplicons of the variable-region-coding DNA sequences with unique nucleic acid identifiers to associate the variable-region-coding DNA sequences derived from individual ones of the subset of the antibody-secreting cells at operation 240, analyzing antibody-type distribution in a natural immune response at operation 245, synthesizing antibodies from the variable-region-coding DNA sequences to form synthetic antibodies at operation 250, and mixing the synthetic antibodies in a proportion equal to the antibody-type distribution in the natural immune response to form the antiserum at operation 255. The exemplary method may conclude with an optional step of validating neutralization properties of the antiserum at operation 260.

Figure 5:
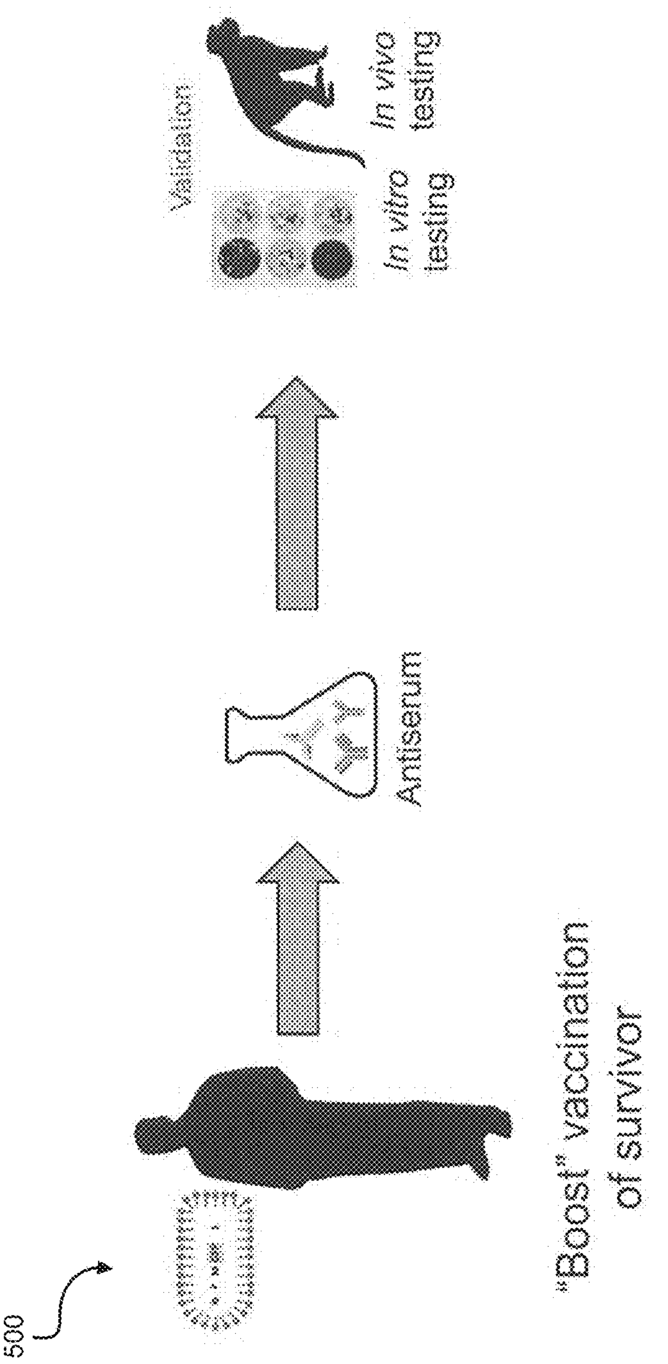
FIG. 5 illustrates an overview of boosting the natural immune response in the test subject according to an example embodiment.
Figure 6:
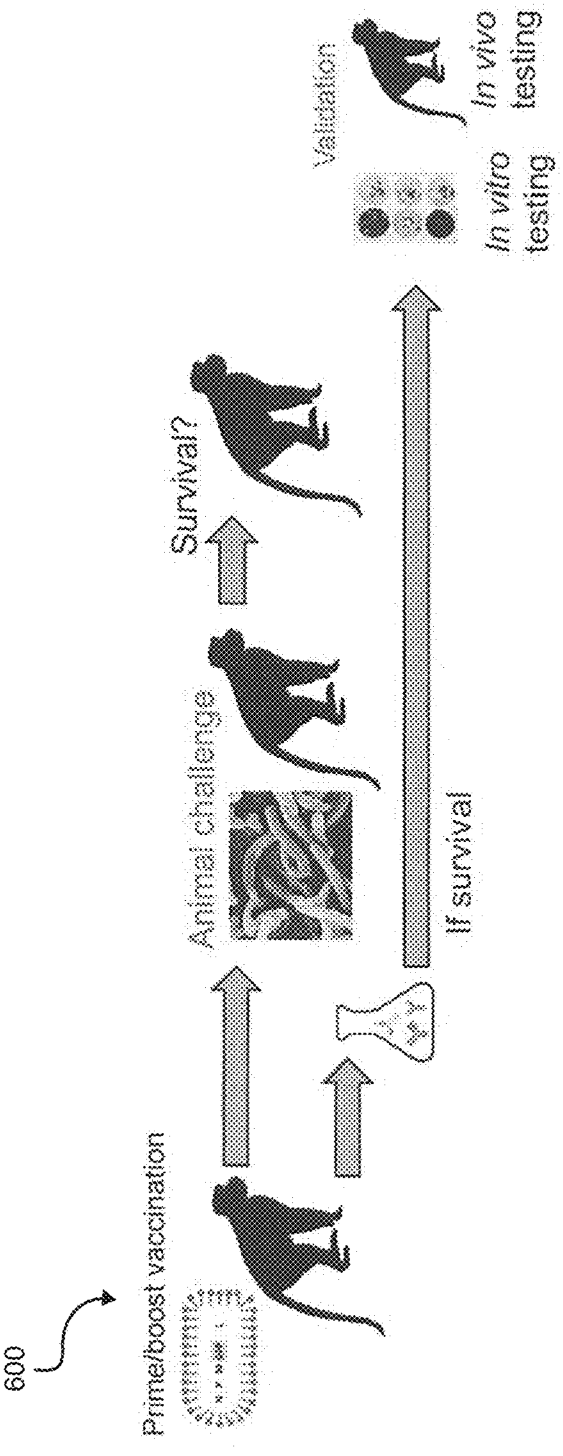
FIG. 6 illustrates an overview of challenging the natural immune response in the test subject according to an example embodiment.

As previously mentioned, the method may further comprise an initial operation of priming the antibody response in the test subject. In some embodiments, for instance, priming the antibody response in the test subject may comprise vaccinating the test subject or selecting a previously infected test subject. In this regard, a test subject having generated a successful antibody response due to exposure either to the target biological agent or to a vaccine may be selected. In some embodiments, for example, the immune response of the test subject may be boosted by providing, for instance, exposure to the target biological agent via a booster vaccine or direct exposure. FIG. 5, for example, illustrates an overview of boosting the natural immune response in the test subject according to an example embodiment. As shown in FIG. 5, the overview 500 includes boosting the vaccination of a survivor test subject, synthesizing the antiserum, and validating the antiserum with in vitro and in vivo testing. In further embodiments, for instance, the immune response of a test subject may be challenged prior to collection such that high confidence antisera may be synthesized. FIG. 6, for example, illustrates an overview of challenging the natural immune response in the test subject according to an example embodiment. As shown in FIG. 6, the overview 600 includes priming and/or boosting vaccination in a test subject, challenging the immune response of the test subject by exposing the test subject to the target biological agent, and determining whether the test subject survives the immune challenge. If the test subject survives the immune challenge, then antisera may be synthesized validated with in vitro and in vivo testing.

Figure 3:
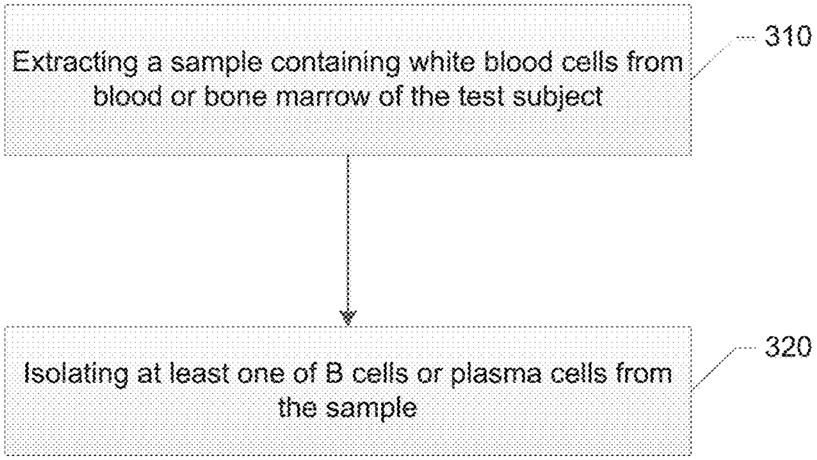
FIG. 3 illustrates a block diagram of collecting the antibody-secreting cells from the test subject according to an example embodiment.

FIG. 3, for instance, illustrates a block diagram of collecting the antibody-secreting cells from the test subject according to an example embodiment. As shown in FIG. 3, collecting the antibody-secreting cells from the test subject may include extracting a sample containing white blood cells from blood or bone marrow of the test subject at operation 310, and isolating at least one of B cells or plasma cells from the sample at operation 320. Plasma cells may be extracted using any suitable extraction means, including, but not limited to, CD138+ Plasma Cell Isolation Kit from Miltenyi Biotec. In this regard, a sample may be extracted from a test subject that has recently been exposed or re-exposed to the target biological agent or a vaccine candidate and, as a result of such exposure, has generated a successful antibody response, as validated via testing as previously described. As a result, by using both memory B cells and plasma cells, the antiserum may comprise a synthetic cocktail of antibodies that mirrors the natural antibody response that may be as therapeutic as a more accurate duplication of the natural response.

Figure 4:
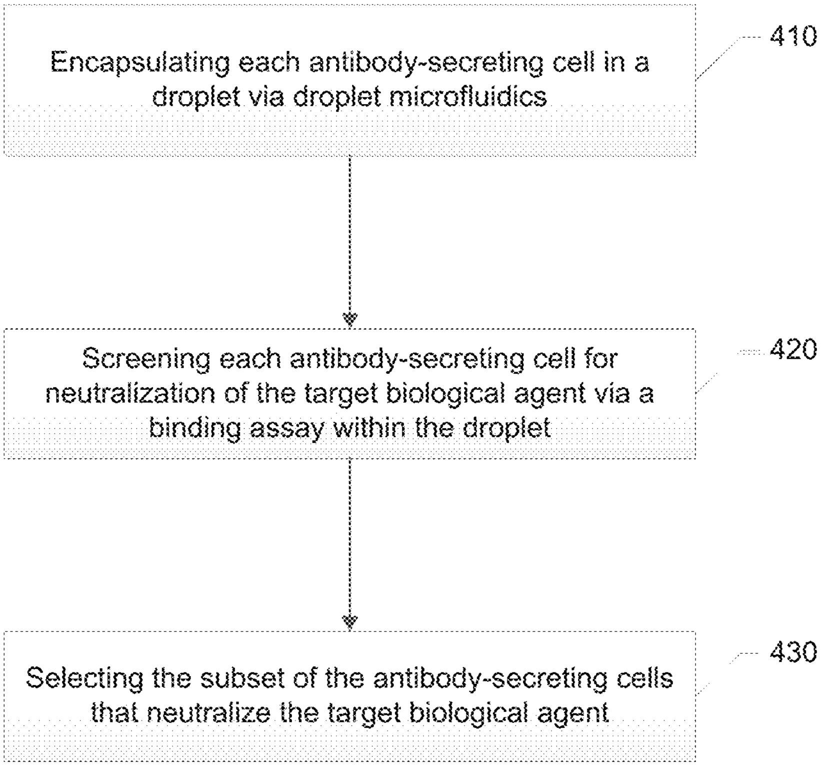
FIG. 4 illustrates a block diagram of selecting the subset of the antibody-secreting cells according to an example embodiment.

FIG. 4, for example, illustrates a block diagram of selecting the subset of the antibody-secreting cells according to an example embodiment. As shown in FIG. 4, selecting the subset of the antibody-secreting cells may include encapsulating each antibody-secreting cell in a droplet via droplet microfluidics at operation 410, screening each antibody-secreting cell for neutralization of the target biological agent via a binding assay within the droplet at operation 420, and selecting the subset of the antibody-secreting cells that neutralize the target biological agent at operation 430. For instance, in some embodiments, the subset of antibody-secreting cells can then, for instance, be rapidly isolated using droplet microfluidic technology in order to obtain, by way of example only, human Ebola virus neutralizing antibody gene sequences. By utilizing droplet microfluidics techniques, no more than one plasma cell may be encapsulated in a droplet in culture media, thereby allowing the secretion of antibody that is contained within the droplet. Functional assays in a droplet microfluidics format using a sorter chip can isolate B cells and/or plasma cells in blood and bone marrow, for example, which secrete human Ebola virus neutralizing antibodies. Such functional assays may include, but are not limited to, bead-based fluorescent antigen concentration assays and/or in-drop viral neutralization assays. Compartmentalization of single cells in microfluidic droplets enables the analysis of proteins released from or secreted by cells. Secreted antibodies can be detected rapidly, for example, by co-compartmentalizing test subject sample cells, a fluorescent probe, and single beads coated with target biological agent neutralizing antibodies in droplets. The beads capture the secreted antibodies, and when the captured antibodies bind to the probe, the fluorescence becomes localized on the beads, thereby generating a clearly distinguishable fluorescence signal that enables droplet sorting. The microfluidic system described can be easily adapted for screening other intracellular, cell-surface, or secreted proteins and for quantifying catalytic or regulatory activities.

In accordance with certain exemplary embodiments, for example, generating variable-region-coding DNA sequences from the antibodies that neutralize the target biological agent may comprise deriving the unique protein sequences for heavy-chain and light-chain variable regions of an antibody species. To generate the variable-coding-region DNA sequences, the reverse transcription polymerase chain reaction (RT-PCR) may be performed on mRNA as part of a second-generation or next-generation sequencing method. The so-called "second-generation sequencing" or "next-generation sequencing" (NGS) techniques have emerged as alternatives to Sanger and dye-terminator sequencing methods and can be beneficially utilized in certain embodiments according to the present invention. NGS methods share the common feature of massively parallel, high-throughput strategies, with the goal of lower costs in comparison to older sequencing methods. NGS methods can be broadly divided into those that require template amplification and those that do not. Amplification-requiring methods include pyrosequencing commercialized by Roche as the 454 technology platforms (e.g., GS 20 and GS FLX), the Solexa platform commercialized by Illumina, and the Supported Oligonucleotide Ligation and Detection (SOLiD) platform commercialized by Applied Biosystems. Non-amplification approaches, also known as single-molecule sequencing, are exemplified by the HELISCOPE® platform commercialized by Helicos BioSciences, and emerging platforms commercialized by VisiGen, Oxford Nanopore Technologies Ltd., and Pacific Biosciences, respectively.

In pyrosequencing, template DNA is fragmented, end-repaired, ligated to adaptors, and clonally amplified in-situ by capturing single template molecules with beads bearing oligonucleotides complementary to the adaptors. Each bead bearing a single template type is compartmentalized into a water-in-oil microvesicle, and the template is clonally amplified using a technique referred to as emulsion PCR. The emulsion is disrupted after amplification and beads are deposited into individual wells of a picotitre plate functioning as a flow cell during the sequencing reactions. Ordered, iterative introduction of each of the four dNTP reagents occurs in the flow cell in the presence of sequencing enzymes and luminescent reporter such as luciferase. In the event that an appropriate dNTP is added to the 3' end of the sequencing primer, the resulting production of ATP causes a burst of luminescence within the well, which is recorded using a CCD camera. It is possible to achieve read lengths greater than or equal to 400 bases, and $1\times10^6$ sequence reads can be achieved, resulting in up to 500 million base pairs (Mb) of sequence. In accordance with certain embodiments of the present invention, the methods of the present invention utilize pyrosequencing.

In the Solexa/Illumina platform (e.g., MISEQ® sequencing platform), sequencing data are produced in the form of shorter-length reads. In this method, single-stranded fragmented DNA is end-repaired to generate 5'-phosphorylated blunt ends, followed by Klenow-mediated addition of a single A base to the 3' end of the fragments. A-addition facilitates addition of T-overhang adaptor oligonucleotides, which are subsequently used to capture the template-adaptor molecules on the surface of a flow cell that is studded with oligonucleotide anchors. The anchor is used as a PCR primer, but because of the length of the template and its proximity to other nearby anchor oligonucleotides, extension by PCR results in the "arching over" of the molecule to hybridize with an adjacent anchor oligonucleotide to form a bridge structure on the surface of the flow cell. These loops of DNA are denatured and cleaved. Forward strands are then sequenced with reversible dye terminators. The sequence of incorporated nucleotides is determined by detection of post-incorporation fluorescence, with each fluor and block removed prior to the next cycle of dNTP addition. Sequence read length ranges from 36 nucleotides to over 50 nucleotides with overall output exceeding 1 billion nucleotide pairs per analytical run.

In accordance with certain exemplary embodiments, for instance, the method may include tagging amplicons of the variable-region-coding DNA sequences with unique nucleic acid identifiers to associate the variable-region-coding DNA sequences derived from individual ones of the subset of the antibody-secreting cells. Tagging the sequences enables the preservation of the variable heavy and light chain antibody sequence pairings, which are required for the antibodies to be functional. By isolating individual antibody-secreting cells in droplets via droplet microfluidics techniques, the amplicons may be tagged with the unique nucleic acid identifiers (i.e. barcodes) to associate all sequences derived from individual droplets and, by extension, individual cells.

In accordance with certain exemplary embodiments, for instance, the method may include analyzing antibody-type distribution in a natural immune response. In such embodiments, for example, the distribution of antibody types in a natural immune response may be estimated by counting the number of cells analyzed that have each genetic sequence, assuming that each plasma cell produces and secretes a roughly equal number of antibody molecules. The proportion of the total cells analyzed for each sequence may be representative of the proportion of the respective antibodies in the antiserum. In this regard, the baseline formulation of an antiserum may be the inclusion of all antibodies that comprise at least 1% of all plasma cells selected; however, this threshold level may be lowered or raised to formulate more complex or less complex mixtures. Similarly, alternative formulations may be based on analysis of antibody-epitope binding using available techniques (e.g., phage display or surface plasmon resonance) to approximate the distribution of binding sites bound by the constituent antibodies in the synthetic antiserum.

According to certain exemplary embodiments, for example, to synthesize the antibodies, traditional antibody synthesis approaches, such as transfecting antibody-sequence-containing plasmids into CHO cells in separate batches for each antibody, may be used. The antiserum may then be created by mixing the synthesized antibodies in the appropriate proportions based on the antibody-type distribution in a natural immune response. Alternatively, the antibody mixture may be produced directly by, for example, transfecting a heterogeneous library of bicistronic lentiviral vectors or plasmids, thereby expressing both heavy and light chains of the antibody CHO cells. In such embodiments, for instance, the composition of the lentivirus or plasmid library may be designed to produce the desired antibody distributions in the final mixture. Any consistent transfection and production efficiency differences between lentivirus vectors or plasmids may be characterized and/or modeled to adjust the composition of the plasmid library to result in the desired proportions of constituent antibodies. In this regard, having both heavy and light chain genes on the same plasmid may guarantee that the secreted antibody has the correct pairing of antibody variable regions. Alternatively, in further embodiments, for example, a complex mixture of fragment antigen-binding (Fab) fragments of the antibody may be used as a therapeutic.

In accordance with certain exemplary embodiments, for instance, the test subject may comprise a human or a non-human animal. In some embodiments, for example, the test subject may comprise a non-human mammal. In further embodiments, for instance, the test subject may comprise a non-human primate. As such, according to certain embodiments, for example, test subjects may include, but are not limited to, humans, mice, rabbits, monkeys, apes, or any other suitable animal for generating antiserum for a target biological agent as understood by one of ordinary skill in the art. In this regard, the test subject may be selected so as to emulate an animal immune response, a human vaccine response, or a recovered human patient antibody repertoire.

According to certain embodiments, the target biological agent may comprise at least one of a virus, a bacterium, a prion, a toxin, a cancer, or any combination thereof. For example, the target biological agent may comprise a virus including, but not limited to, a flavivirus, an alphavirus, a bromovirus, an arterivirus, an aphthovirus, a rhinovirus, a hepatovirus, a cardiovirus, a cosavirus, a dicipivirus, an erbovirus, a kobuvirus, a megrivirus, a parechovirus, a piscevirus, a salivirus, a sapelovirus, a senecavirus, a teschovirus, a tremovirus, a potyvirus, a coronavirus, a norovirus, an orthomyxovirus, a rotavirus, a picobirnavirus, an enterovirus, a bymovirus, a comovirus, a nepovirus, a nodavirus, a picornavirus, a sobemovirus, a luteovirus, a carmovirus, a dianthovirus, a pestivirus, a tombusvirus, a bacteriophage, a carlavirus, a furovirus, a hordeivirus, a potexvirus, a rubivirus, a tobravirus, a tricornavirus, a tymovirus, and/or the like. In further embodiments, for example, the target biological agent may comprise a virus including, but not limited to, dengue virus (e.g., DENV1, DENV2, DENV3, DENV4), West Nile virus, absettarov virus, alkhurma virus, deer tick virus, gadgets gully virus, kadam virus, karshi virus, kyasanur forest disease virus, Langat virus, louping ill virus, omsk hemorrhagic fever virus, powassan virus, royal farm virus, sokuluk virus, tick-borne encephalitis virus, Turkish sheep encephalitis virus, kama virus, meaban virus, Saumarez Reef virus, tyuleniy virus, Aedes flavivirus, barkedji virus, calbertado virus, cell fusing agent virus, chaoyang virus, culex flavivirus, culex theileri flavivirus, donggang virus, ilomantsi virus, Kamiti River virus, lammi virus, marisma mosquito virus, nakiwogo virus, nhumirim virus, nounane virus, Spanish culex flavivirus, Spanish ochlerotatus flavivirus, quang binh virus, aroa virus, bussuquara virus, kedougou virus, cacipacore virus, koutango virus, ilheus virus, Japanese encephalitis virus, Murray Valley encephalitis virus, alfuy virus, rocio virus, St. Louis encephalitis virus, usutu virus, yaounde virus, kokobera virus, bagaza virus, baiyangdian virus, duck egg drop syndrome virus, Jiangsu virus, Israel turkey meningoencephalomyelitis virus, ntaya virus, tembusu virus, zika virus, banzi virus, bouboui virus, edge hill virus, jugra virus, saboya virus, sepik virus, Uganda S virus, wesselsbron virus, yellow fever virus, Entebbe bat virus, yokose virus, apoi virus, vowbone ridge virus, Jutiapa virus, modoc virus, sal vieja virus, san perlita virus, bukalasa bat virus, Carey Island virus, Dakar bat virus, Montana myotis leukoencephalitis virus, Phnom Penh bat virus, Rio Bravo virus, soybean cyst nematode virus 5, Aedes cinereus flavivirus, Aedes vexans flavivirus, Coxsackievirus, echovirus, Enterovirus A, Enterovirus B, Enterovirus C, Enterovirus D, Enterovirus E, Enterovirus F, Enterovirus G, Enterovirus H, Enterovirus J, Rhinovirus A, Rhinovirus B, Rhinovirus C, poliovirus, bovine viral diarrhea virus, sindbis virus, hepatitis C, Barmah Forest virus, eastern equine encephalitis virus, Middelburg virus, ndumu virus, bebaru virus, chikungunya virus, mayaro virus, una virus, o'nyong nyong virus, Igbo-Ora virus, Ross River virus, getah virus, sagiyama virus, Semliki Forest virus, me tri virus, cabassou virus, Everglades virus, mosso das pedras virus, mucambo virus, paramana virus, pixuna virus, Rio Negro virus, trocara virus, Bijou Bridge virus, Venezuelan equine encephalitis virus, aura virus, babanki virus, kyzylagach virus, ockelbo virus, whataroa virus, Buggy Creek virus, Fort Morgan virus, Highlands J virus, western equine encephalitis virus, salmon pancreatic disease virus, sleeping disease virus, southern elephant seal virus, tonate virus, Brome mosaic virus, equine arteritis virus, foot-and-mouth disease virus, bovine rhinitis A virus, bovine rhinitis B virus, equine rhinitis A virus, aquamavirus A, duck hepatitis A virus, encephalomyocarditis virus, theilovirus, cosavirus A, cadicivirus A, equine rhinitis B virus, hepatitis A virus, aichivirus A, aichivirus B, aichivirus C, melegrivirus A, human parechovirus, Ljungan virus, fathead minnow picornavirus, salivirus A, porcine sapelovirus, simian sapelovirus, avian sapelovirus, Seneca Valley virus, porcine teschovirus, avian encephalomyelitis virus, potato virus A, SARS, Human coronavirus 229E, Human coronavirus OC43, New Haven coronavirus, Human coronavirus HKU1, Middle East respiratory syndrome coronavirus, infectious bronchitis virus, porcine coronavirus, bovine coronavirus, feline coronavirus, canine coronavirus, turkey coronavirus, ferret enteric coronavirus, ferret systemic coronavirus, pantropic canine coronavirus, porcine epidemic diarrhea virus, Ebola virus, measles virus, Influenza virus A, Influenza virus B, Influenza virus C, isavirus, thogotovirus, quaranjavirus, Norwalk virus, Hawaii virus, Snow Mountain virus, Mexico virus, Desert Shield virus, Southampton virus, Lordsdale virus, Wilkinson virus, bluetongue virus, hepatitis E virus, apple chlorotic leaf spot virus, beet yellows virus, Rubella virus, Marburg virus, Mumps virus, Nipah virus, Hendra virus, RSV, NDV, Rabies virus, Nyavirus, Lassa virus, Hantavirus, Crimean-Congo hemorrhagic fever, hepatitis D virus, Nyamanini virus, Midway virus, and/or the like.

In other embodiments, for instance, the target biological agent may comprise a bacterium including, but not limited to, *Salmonella typhi, Rickettsia prowazekii, Rickettsia typhi, Orientia tsutsugamushi, Rickettsia australis, Streptococcus pneumonia, Haemophilus influenza, Streptococcus pyogenes, Neisseria meningitides, Bacillus anthracis, Clostridium tetani, Mycobacterium tuberculosis, Mycobacterium bovis, Bordetella pertussis, Vibrio cholera, Corynebacterium diphtheria, Clostridium botulinum*, and/or the like. In further embodiments, for example, the target biological agent may comprise a prion. In such embodiments, for instance, the antiserum may be synthesized as therapy for a disease caused by prions including, but not limited to, scrapie, bovine spongiform encephalopathy, transmissible mink encephalopathy, chronic wasting disease, feline spongiform encephalopathy, exotic ungulate encephalopathy, spongiform encephalopathy, Creutzfeldt-Jakob disease, Gerstmann-Sträussler-Scheinker syndrome, fatal familial insomnia, kuru, multiple system atrophy, and/or the like. In some embodiments, for instance, the target biological agent may comprise a toxin including, but not limited to, a venom, a poison, any other biotoxin and/or the like. For example, the venom may comprise venom derived from spiders, centipedes, scorpions, stinging insects (e.g., bees, wasps, etc.), caterpillars, ants, true bugs, jellyfish (e.g., box jellyfish), cone snails, coleoids, cartilaginous fish (e.g., stingrays, sharks, chimaeras, etc.), teleost fish (e.g., onejaws, catfish, stonefish, waspfish, scorpionfish, lionfish, etc.), salamandrid salamanders, snakes, Mexican beaded lizards, gila monsters, monitor lizards, Komodo dragons, solenodons, shrews, platypi, and/or the like.

II. Method for Mitigating Effects of a Target Biological Agent

In another aspect, the present invention provides for methods for mitigating effects of a target biological agent on an affected subject. For instance, this method may provide, for example, an affordable and efficient manner for generating antisera that provide protection and treatment against a target biological agent while also replicating the natural immune response (including, for example, antibody dependent cell-mediated cytotoxicity and/or the like) to that target biological agent in a healthy individual. In general, methods for mitigating effects of a target biological agent on an affected subject may include synthesizing an antiserum for rapid-turnaround therapies and administering the antiserum to the affected subject in need thereof. In certain embodiments, synthesizing the antiserum may comprise collecting antibody-secreting cells from a test subject, wherein the test subject has been exposed to a target biological agent and has produced an antibody response; selecting a subset of the antibody-secreting cells, the subset of the antibody-secreting cells producing antibodies that neutralize the target biological agent; generating variable-region-coding DNA sequences from the antibodies that neutralize the target biological agent; tagging amplicons of the variable-region-coding DNA sequences with unique nucleic acid identifiers to associate the variable-region-coding DNA sequences derived from individual ones of the subset of the antibody-secreting cells; analyzing antibody-type distribution in a natural immune response; synthesizing antibodies from the variable-region-coding DNA sequences to form synthetic antibodies; and mixing the synthetic antibodies in a proportion equal to the antibody-type distribution in the natural immune response to form the antiserum. As such, the antiserum may be formed according to any of the embodiments disclosed in regard to the method for synthesizing an antiserum for rapid-turnaround therapies.

Figure 7:
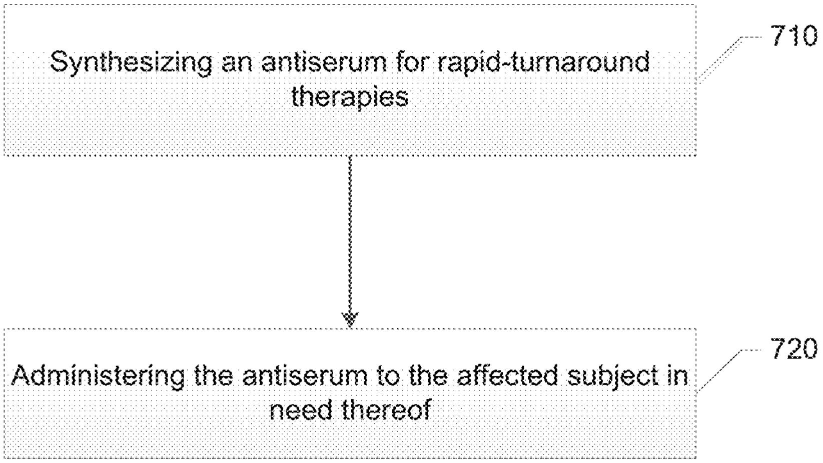
FIG. 7 illustrates a block diagram of mitigating effects of a target biological agent in an affected subject according to an example embodiment.

FIG. 7, for example, illustrates a block diagram of mitigating effects of a target biological agent in an affected subject according to an example embodiment. As shown in FIG. 7, mitigating effects of a target biological agent on an affected subject comprises an initial operation 710 of synthesizing an antiserum for rapid-turnaround therapies. The method for synthesizing the antiserum is illustrated in FIGS. 1-6. The method further comprises operation 720, which comprises administering the antiserum from operation 710 to the affected subject in need thereof.

Exemplary Embodiments

Certain exemplary embodiments provide a method for synthesizing an antiserum for rapid-turnaround therapies. For instance, this method provides an affordable and efficient manner for generating antisera that provide protection and treatment against a target biological agent while also replicating the natural immune response (including, for example, antibody dependent cell-mediated cytotoxicity and/or the like) to that target biological agent in a healthy individual. In one aspect, the method for synthesizing an antiserum for rapid-turnaround therapies includes collecting antibody-secreting cells from a test subject, wherein the test subject has been exposed to a target biological agent and has produced an antibody response; selecting a subset of the antibody-secreting cells, the subset of the antibody-secreting cells producing antibodies that neutralize the target biological agent; generating variable-region-coding DNA sequences from the antibodies that neutralize the target biological agent; tagging amplicons of the variable-region-coding DNA sequences with unique nucleic acid identifiers to associate the variable-region-coding DNA sequences derived from individual ones of the subset of the antibody-secreting cells; analyzing antibody-type distribution in a natural immune response; synthesizing antibodies from the variable-region-coding DNA sequences to form synthetic antibodies; and mixing the synthetic antibodies in a proportion equal to the antibody-type distribution in the natural immune response to form the antiserum.

In accordance with certain exemplary embodiments, collecting the antibody-secreting cells from the test subject comprises extracting a sample containing white blood cells from blood or bone marrow of the test subject, and isolating at least one of B cells or plasma cells from the sample. According to certain embodiments, selecting the subset of the antibody-secreting cells comprises encapsulating each antibody-secreting cell in a droplet via droplet microfluidics, screening each antibody-secreting cell for neutralization of the target biological agent via a binding assay within the droplet, and selecting the subset of the antibody-secreting cells that neutralize the target biological agent.

In accordance with certain exemplary embodiments, the method further comprises an initial operation of priming the antibody response in the test subject. In some embodiments, priming the antibody response in the test subject comprises vaccinating the test subject or selecting a previously infected test subject. According to certain embodiments, the method further comprises challenging the natural immune response in the test subject after priming the antibody response in the test subject and prior to collecting the antibody-secreting cells from the test subject. In further embodiments, the method further comprises boosting the natural immune response in the test subject. In other embodiments, the method further comprises validating neutralization properties of the antiserum after synthesis.

In accordance with certain exemplary embodiments, the test subject comprises a human or a non-human animal. According to certain embodiments, the target biological agent comprises at least one of a virus, a bacterium, a prion, a toxin, a cancer, or any combination thereof.

In another aspect, certain exemplary embodiments provide a method for mitigating effects of a target biological agent on an affected subject. For instance, this method provides for the administration of antisera that provide protection and treatment against a target biological agent while also replicating the natural immune response (including, for example, antibody dependent cell-mediated cytotoxicity and/or the like) to that target biological agent in a healthy individual. According to certain embodiments, the method includes synthesizing an antiserum for rapid-turnaround therapies and administering the antiserum to the affected subject in need thereof. In some embodiments, synthesizing the antiserum comprises collecting antibody-secreting cells from a test subject, wherein the test subject has been exposed to a target biological agent and has produced an antibody response; selecting a subset of the antibody-secreting cells, the subset of the antibody-secreting cells producing antibodies that neutralize the target biological agent; generating variable-region-coding DNA sequences from the antibodies that neutralize the target biological agent; tagging amplicons of the variable-region-coding DNA sequences with unique nucleic acid identifiers to associate the variable-region-coding DNA sequences derived from individual ones of the subset of the antibody-secreting cells; analyzing antibody-type distribution in a natural immune response; synthesizing antibodies from the variable-region-coding DNA sequences to form synthetic antibodies; and mixing the synthetic antibodies in a proportion equal to the antibody-type distribution in the natural immune response to form the antiserum.

In accordance with certain exemplary embodiments, collecting the antibody-secreting cells from the test subject comprises extracting a sample containing white blood cells from blood or bone marrow of the test subject, and isolating at least one of B cells or plasma cells from the sample. According to certain embodiments, selecting the subset of the antibody-secreting cells comprises encapsulating each antibody-secreting cell in a droplet via droplet microfluidics, screening each antibody-secreting cell for neutralization of the target biological agent via a binding assay within the droplet, and selecting the subset of the antibody-secreting cells that neutralize the target biological agent.

In accordance with certain exemplary embodiments, the method further comprises an initial operation of priming the antibody response in the test subject. In some embodiments, priming the antibody response in the test subject comprises vaccinating the test subject or selecting a previously infected test subject. According to certain embodiments, the method further comprises challenging the natural immune response in the test subject after priming the antibody response in the test subject and prior to collecting the antibody-secreting cells from the test subject. In further embodiments, the method further comprises boosting the natural immune response in the test subject. In other embodiments, the method further comprises validating neutralization properties of the antiserum after synthesis.

In accordance with certain exemplary embodiments, the test subject comprises a human or a non-human animal. According to certain embodiments, the target biological agent comprises at least one of a virus, a bacterium, a prion, a toxin, a cancer, or any combination thereof.

Many modifications and other embodiments will come to mind to one skilled in the art to which this disclosure pertains having the benefit of the teachings presented in the foregoing descriptions and the associated drawings. Therefore, it is to be understood that this disclosure is not to be limited to the specific embodiments disclosed and that modifications and other embodiments are intended to be included within the scope of the appended claims. Moreover, although the foregoing descriptions and the associated drawings describe exemplary embodiments in the context of certain exemplary combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. In cases where advantages, benefits or solutions to problems are described herein, it should be appreciated that such advantages, benefits and/or solutions may be applicable to some example embodiments, but not necessarily all example embodiments. Thus, any advantages, benefits or solutions described herein should not be thought of as being critical, required or essential to all embodiments or to that which is claimed herein. Although specific terms are employed herein, they are used in a generic and descriptive sense only and not for purposes of limitation.

What is claimed is:

1. A method for synthesizing an antiserum for rapid-turnaround therapies, the method comprising:

collecting antibody-secreting cells from a test subject, wherein the test subject has been exposed to a target biological agent and has produced a successful antibody response;

selecting a subset of the antibody-secreting cells, the subset of the antibody-secreting cells producing antibodies that neutralize the target biological agent;

generating variable-region-coding DNA sequences from the antibodies that neutralize the target biological agent;

tagging amplicons of the variable-region-coding DNA sequences with unique nucleic acid identifiers to associate the variable-region-coding DNA sequences derived from individual ones of the subset of the antibody-secreting cells;

analyzing antibody-type distribution in a natural immune response;

synthesizing antibodies from the variable-region-coding DNA sequences to form synthetic antibodies; and mixing the synthetic antibodies in a proportion equal to the antibody-type distribution in the natural immune response to form the antiserum.

2. The method according to claim 1, wherein collecting the antibody-secreting cells from the test subject comprises:

extracting a sample containing white blood cells from blood or bone marrow of the test subject; and isolating at least one of B cells or plasma cells from the sample.

3. The method according to claim 1, wherein selecting the subset of the antibody-secreting cells comprises:

encapsulating each antibody-secreting cell in a droplet via droplet microfluidics;

screening each antibody-secreting cell for neutralization of the target biological agent via a binding assay within the droplet; and selecting the subset of the antibody-secreting cells that neutralize the target biological agent.

4. The method according to claim 1, further comprising an initial operation of priming the antibody response in the test subject.

5. The method according to claim 4, wherein priming the antibody response in the test subject comprises vaccinating the test subject or selecting a previously infected test subject.

6. The method according to claim 5, further comprising boosting the natural immune response in the test subject.

7. The method according to claim 4, further comprising challenging the natural immune response in the test subject after priming the antibody response in the test subject and prior to collecting the antibody-secreting cells from the test subject.

8. The method according to claim 1, further comprising validating neutralization properties of the antiserum after synthesis.

9. The method according to claim 1, wherein the test subject comprises a human or a non-human animal.

10. The method according to claim 1, wherein the target biological agent comprises at least one of a virus, a bacterium, a prion, a toxin, a cancer, or any combination thereof.

* * * * *